United States Patent [19]

Allen, Jr. et al.

[11] Patent Number: 4,515,791
[45] Date of Patent: May 7, 1985

[54] SUBSTITUTED PHENYL-1,2,4-TRIAZOLO[2,3-b]PYRIDAZIN-3(2H)ONES AS ANTI-ASTHMA AGENTS

[75] Inventors: George R. Allen, Jr., Old Tappan, N.J.; John W. Hanifin, Jr.; Daniel B. Moran, both of Suffern, N.Y.; Jay D. Albright, Nanuet, N.Y.

[73] Assignee: American Cyanamid Company, Stamford, Conn.

[21] Appl. No.: 273,818

[22] Filed: Jun. 15, 1981

Related U.S. Application Data

[63] Continuation-in-part of Ser. No. 156,009, Jun. 3, 1980, abandoned.

[51] Int. Cl.³ ............... C07D 487/04; A61K 31/50
[52] U.S. Cl. .................... 514/248; 544/236; 514/826
[58] Field of Search ............ 424/250; 544/236

[56] References Cited

U.S. PATENT DOCUMENTS 4,112,095  9/1978  Allen, Jr. .............. 544/236

OTHER PUBLICATIONS

Petrovana et al, Chem. Abs., 89, 163524a (1977).
Maki et al., Chem. Abs., 83, 193361p (1975).

*Primary Examiner*—Mark L. Berch
*Attorney, Agent, or Firm*—Edward A. Conroy, Jr.

[57] ABSTRACT

Substituted phenyl-1,2,4-triazolo[4,3-b]pyridazin-3(2H)-ones, useful as anti-asthma agents.

3 Claims, No Drawings

SUBSTITUTED PHENYL-1,2,4-TRIAZOLO[2,3-b]PYRIDAZIN-3(2H)ONES AS ANTI-ASTHMA AGENTS

CROSS REFERENCE TO RELATED APPLICATION

This application is a continuation-in-part of our copending application Ser. No. 156,009, filed June 3, 1980, now abandoned.

DESCRIPTION OF THE INVENTION

This invention is concerned with new compounds of the formula:

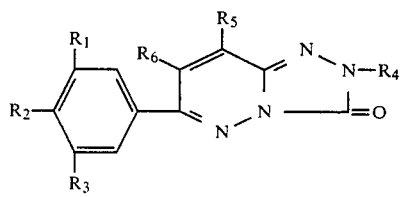

wherein $R_1$, $R_2$ and $R_3$ are each individually selected from the group consisting of hydrogen, cyano, nitro, trifluoromethyl, bromo, fluoro, chloro, amino, alkoxy ($C_1$–$C_6$) and thiocarbamoyl with the proviso that at least one of $R_1$, $R_2$ and $R_3$ must be other than hydrogen; and $R_4$, $R_5$ and $R_6$ are each individually selected from the group consisting of hydrogen and alkyl ($C_1$–$C_6$).

The compounds of the present invention may be prepared by treating an appropriately substituted chloropyridazine (1) with an ethyl carbazate (2) in butanol at reflux for 8–72 hours, cooling the reaction mixture in ice and recovering the products (3), which are then treated with a base such as sodium hydride and alkyl halide giving (4), wherein $R_1$, $R_2$, $R_3$, $R_4$, $R_5$ and $R_6$ are as hereinabove defined, as illustrated below.

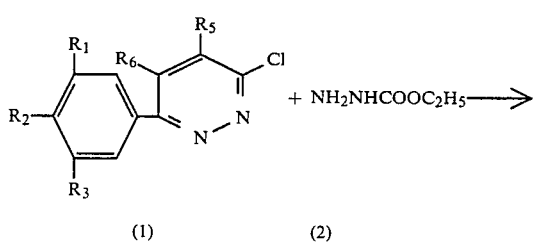

(1)      (2)

-continued

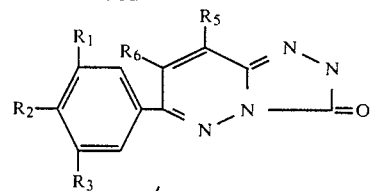

(3)

base (NaH)
$R_4X$ (X = Br, I)

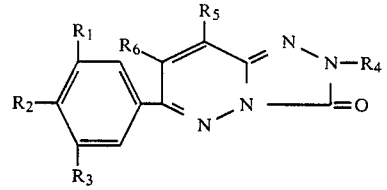

(4)

These compounds are effective in treating asthma in warm-blooded animals as determined by the folllowing test which measures anti-asthma activity by the mouse passive cutaneous anaphylaxis (PCA) test.

Preparation of Immunoglobulin G (IgG)

Female Swiss Webster mice (Buckberg) were immunized by intraperitoneal injection of 10 mg. ovalbumin (Miles Lab. Code 95051, Batch 21) in 0.5 ml. of 50% saline-50% Freunds complete adjuvant (Difco Lab.). The mice were boosted with the same antigen preparation one and two weeks later. Forty days after the original immunization the mice were sacrificed by decapitation and serum collected. The serum was pooled, heated at 56° C. for 4 hours and titered to obtain a 2 hour PCA lesion slightly greater than one cm. in diameter. The challenge was 0.1 mg. DNP-ovalbumin.

Preparation of Immunoglobulin E (IgE)

Female B6×D2 F1 mice (Jackson Labs.) were given an intraperitoneal injection of 0.5 ml. of saline with one $\mu$g of dinitrophenylated ovalbumin and one mg. aluminum hydroxide gel (Wyeth Amphogel). Preparation of the DNP-ovalbumin (approx. 2 DNP/molecule) is described in the next paragraph. One and two months later the mice were boosted with the same antigen preparation. One week after the second boost, the mice were sacrificed by decapitation and serum collected. The serum was pooled and titered to obtain a 48 hour PCA lesion slightly greater than one cm. in diameter.

Preparation of DNP-ovalbumin

One gram of ovalbumin, 1.0 g. of potassium carbonate and 1.0 g. of dinitrobenzene sulfonic acid were dissolved in 50 ml. of water. The solution was shaken for 18 hours at 37° C. and then placed in a cellophane dialysis bag and dialysed versus three changes of 0.9% saline at 4° C. The protein concentration was determined by the method of Lowry, et al., J. Biol. Chem., 193, 265 (1951). The content of DNP groups was determined from the absorbance at 365 nm. (extinction coefficient = 18500). The DNP-ovalbumin prepared by this method contained $4.4 \times 10^{-5}$ moles of DNP/gram of protein or 1.9 residues per ovalbumin molecule.

Passive Cutaneous Anaphylaxis Test

At −50 hour (relative to antigen challenge at 0 hour) 50 μl. of IgE is injected intradermally on the left side of 25 g. female mouse, posterior to the axilla at the level of the diaphragm. At −2 hour, 50 μl. of IgG is injected intradermally on the right side of the mouse. The mice are then placed in individual cages and randomly assigned to control or treatment groups. Challenge and reading are performed in serial order so that reading of the assay is essentially blind. At −1 hour, the control animals received an intraperitoneal injection of 0.5 ml. of a 0.05% solution of carboxymethylcellulose in saline. For treatment animals, the test compound is dissolved or suspended in the carboxymethylcellulose-saline solution and administered intraperitoneally at −1 hour at 2, 10 or 50 mg./kg. At 0 hour, the mice are anesthetized with ether and 0.5 ml. of saline containing 0.1 mg. of DNP-ovalbumin antigen and 2.5 mg. of Evans blue dye is injected into the tail vein. At +15 minutes the mice are sacrificed by cervical dislocation, the dorsal skin is removed and the blue PCA spots are examined on the inside surface. The largest and smallest diameters of the lesion and a qualitative estimate of intensity of color are recorded. The mean of the products of diameters (area) for mice in a given treatment group are compared with the control group. IgE and IgE lesions are analyzed independently. If the area for a treatment group is significantly smaller than the lesion area for the control group for either IgE or IgG lesion, the test compound is considered to be active as an anti-asthma agent. The results for typical compounds of this invention appear in Table I below.

TABLE I

| Compound | Result |
| --- | --- |
| p-(2,3-Dihydro-7-methyl-3-oxo-1,2,4-triazolo[4,3-b]pyridazin-6-yl)benzonitrile | Active |
| 7-Methyl-6-(m-nitrophenyl)-1,2,4-triazolo[4,3-b]pyridazin-3(2H)—one | Active |
| p-(2,3-Dihydro-7-methyl-3-oxo-1,2,4-triazolo[4,3-b]pyridazin-6-yl)thiobenzamide | Active |
| 2,7-Dimethyl-6-(m-nitrophenyl)-1,2,4-triazolo[4,3-b]pyridazin-3(2H)—one | Active |
| 6-(m-Aminophenyl)-2,7-dimethyl-1,2,4-triazolo[4,3-b]pyridazin-3(2H)—one | Active |

Another test which determines anti-asthma activity is by measuring the inhibition of histamine release from human blood basophils as described below.

Reagents

8% Perchloric Acid

A 100 ml. portion of 60% perchloric acid is added to 650 ml. of water.

Human Albumin

Sigma Chemical Co.

Calcium and Magnesium Stocks

Made to 0.075M. and 0.5M. respectively using calcium chloride dihydrate and magnesium chloride hexahydrate.

10× Concentrated Tris Buffer

Contains 140.3 g. of sodium chloride, 7.45 g. of potassium chloride and 74.5 g. of Trizma-Tris Pre-Set, Reagent Grade, pH 7.6, at 25° C. (Sigma Chemical Co.) per 2000 ml. distilled water.

Tris-A Buffer

A 10 ml. portion of 10× concentrated tris buffer and 1.0 ml. of human serum albumin diluted to 100 ml. with water.

Tris-ACM Buffer

A 10 ml. portion of 10× concentrated tris buffer, 1.0 ml. of human serum albumin, 0.8 ml. of calcium stock and 0.2 ml. of magnesium stock, diluted to 100 ml. with water.

Rabbit Antihuman IgE

Behring Diagnostics. Prepared at a 10 μg. protein/ml. concentration.

Ragweed Antigen E

NIH Research Reference Branch. Prepared at a 0.01 μg. protein/ml. concentration.

House Dust Mite Extract (*Dermatophagoides farinae*)

Hollister-Stier Lab. The 1:100 (w:v) allergenic extract is diluted 1:1,000 or 1:10,000 before use.

Other Allergens

Intradermal solutions or intramuscular preparations for hyposensitization. Hollister-Stier Lab. Final concentration is 1 PNU/ml.

Separation of Leukocytes from Human Blood and Challenge

An 80 ml. portion of blood is drawn from humans with known histamine release to anti-IgE, ragweed antigen or other specific allergen, using four 20 ml. heparinized Vacutainer tubes (Becton Dickinson Inc.). The 80 ml. of blood is mixed with 20 ml. of saline containing 0.6 g. of dextrose and 1.2 g. of dextran. The blood is allowed to sediment in two 50 ml. polycarbonate centrifuge tubes until a sharp interface develops between the red cells and plasma (60–90 minutes). The plasma is withdrawn from each tube and transferred to 50 ml. polycarbonate tubes. This plasma is centrifuged at 4° C. and 110× gravity for eight minutes and then the supernatant is removed as completely as possible. The cell button is resuspended in 2 to 3 ml. of Tris-A buffer using a siliconized Pasteur pipet with a bulb attached and drawing the liquid gently in and out of the pipet with the tip below the liquid until an even suspension of cells is obtained. The suspension is then diluted to 50 ml. with Tris-A buffer and centrifuged as described above. Repeat this procedure one more time. The supernatant is removed and the cell button resuspended in 2 to 3 ml. of Tris-ACM buffer and transferred to a polycarbonate flask with additional Tris-ACM buffer. The cells are placed in a 37° C. water bath and uniform suspension is maintained by frequent swirling. The reaction tubes, containing anti-IgE or antigen alone, or anti-IgE or antigen plus test compound in 0.2 ml. total volume are also placed in a 37° C. water bath. One ml. of a uniform suspension of the cells is added to each tube and the tubes are incubated for 60 minutes at 37° C., vortexing the tubes gently every 15 minutes to maintain suspension. The reaction tubes are then centrifuged at 4° C. and 15,000 rmp for 10 minutes. One ml. of the supernatant is decanted into 3 ml. polyethylene tubes and 0.2 ml. of 8% perchloric acid is added to each tube. Blank tubes and total tubes are included in each test. Blank tubes have all the reagents including cells except that which releases histamine (i.e., antigen or anti-IgE). The total tubes are made up by adding 1.0 ml. of cells in triplicate to 0.2 ml. of 8% perchloric acid. The volume is adjusted to equal that of reaction tubes by adding an appropriate amount of Tris-ACM buffer.

Assay of Released Histamine by the Automated Fluorometric Method

This procedure is based on the method of Siraganian, R. P., J. of Immunological Methods, 7, 283, 1975 and is based on the manual method of Shore, P. A. et al., J. of Pharmacology, 127, 182, 1959.

The automated system consists of the following Technicon Autoanalyzer II components: Sampler IV; Dual Speed Proportioning Pump III; Fluoronephelometer with a narrow pass primary filter 7-60 and a secondary filter 3-74; Recorder and Digital Printer. The manifold described by Siraganian (vide supra) is employed with the following modifications: the dialyzer is omitted; all pumping tubes pass through a single proportioning pump with large capacity and twice the volume of sample is taken for analysis. The automated chemistry consists of the following steps: extraction from alkaline saline into butanol; back extraction into dilute hydrochloric acid by addition of heptane; reaction of histamine with o-phthaldialdehyde at high pH and conversion of the o-phthalidialdehyde adduct to a stable fluorophore with phosphoric acid. The reaction product is then passed through the fluorometer. The full scale response is adjusted to 50 ng. histamine base with a threshold sensitivity of approximately 0.5 ng.

Assay of Released Histamine by Isotope Enzyme Assay

This assay method has been described in detail by Snyder et al., Journal of Pharmacology and Experimental Therapeutics, 153, 544 (1966).

A crude preparation of histamine N-methyl transferase is made from guinea pig brain. The supernatant for histamine assay is mixed with 0.2 $\mu$Ci $^3$H-histamine (New England Nuclear Inc.), 0.05 $\mu$Ci $^{14}$C-S-adenosylmethionine (New England Nuclear VNc.) and 50 $\mu$l. of methyl transferase. The mixture is incubated for one hour at 37° C. and the reaction is stopped by the addition of 2 ml. of 1N sodium hydroxide. The solution is then saturated with sodium chloride and the methyl histamine formed is extracted into 6 ml. of chloroform. The organic phase is separated and washed with 2 ml. of 1N sodium hydroxide. The organic phase is poured into a scintillation vial and allowed to evaporate to dryness. A one ml. portion of ethanol is added to dissolve the residue and 10 ml. of Aquasol counting fluid (New England Nuclear Inc.) is added. The vials are counted in a Nuclear Chicago Mark I liquid scintillation counter for both tritium and carbon-14 and the ratio (dpm-$^{14}$C/dpm-$^3$H) is computed. A standard curve of the ratio for several concentrations of histamine (1–200 ng.) is prepared and the amount of histamine in the cell supernatants is read from this curve.

Calculation of the Results of Histamine Release

For fluorometric assays the instrument blank is subtracted from the ng. histamine of each sample.

For isotope assays the $^{14}$C/$^3$H ratio is computed for each sample and the ng. histamine read from a standard curve. Then the ng. histamine of each sample is divided by the mean of the three totals (cells lysed with perchloric acid) to obtain percent release.

Control samples contain antigen but no compound. Blank (or spontaneous release) samples contain neither antigen nor compound. The mean of the blanks (three replicates) is subtracted from the percent release for controls and compounds.

The mean for control and compound groups is computed and the result for a test compound computed as % of control by the formula:

$$\frac{100 \times \% \text{ histamine release with compound}}{\% \text{ histamine release with controls}}$$

A compound is considered active if the IC$_{50}$ (the concentration of compound which inhibits the histamine release by 50%) is 0.1 mM. or less.

The results of this test on representative compounds of this invention appear in Table II.

TABLE II

| Inhibition of Histamine Release from Human Blood Basophils | |
|---|---|
| Compound | Result |
| 6-(p-Bromophenyl)-1,2,4-triazolo[4,3-b]-pyridazin-3(2H)—one | Active |
| 2,7-Dimethyl-6-(m-nitrophenyl)-1,2,4-triazolo[4,3-b]pyridazin-3(2H)—one | Active |
| 6-(p-Bromophenyl)-2-ethyl-7-methyl-1,2,4-triazolo[4,3-b]pyridazin-3(2H)—one | Active |
| 6-(3,4,5-Trimethoxyphenyl)-1,2,4-triazolo[4,3-b]pyridazin-3(2H)—one | Active |
| 6-(3-Fluoro-4-methoxyphenyl)-1,2,4-triazolo[4,3-b]pyridazin-3(2H)—one | Active |
| 6-(3,4-Dichlorophenyl)-1,2,4-triazolo[4,3-b]pyridazin-3(2H)—one | Active |
| 6-(p-Chlorophenyl)-8-methyl-1,2,4-triazolo[4,3-b]pyridazin-3(2H)—one | Active |

The novel compounds of the present invention have thus been found to be highly useful for meliorating asthma when administered in amounts ranging from about 1.0 mg. to about 100.0 mg. per kilogram of body weight per day. A preferred dosage regimen for optimum results would be from about 5.0 mg. to about 50.0 mg. per kilogram of body weight per day, and such dosage units are employed that a total of from about 0.35 g. to about 3.5 g. of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. These active compounds may be administered by oral, intravenous, intramuscular, or subcutaneous routes, and also be inhalation therapy including aerosol sprays.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10 to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparation may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between about 0.1 and 5.0 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1 p-(2,3-Dihydro-7-methyl-3-oxo-1,2,4-triazolo[4,3-b]pyridazin-6-yl)-benzonitrile

A 200 g. portion of 6-p-cyanophenyl-4,5-dihydro-3(2H)-pyridazinone [F. J. McEvoy and G. R. Allen, J. Med. Chem., 17, 281 (1974); W. V. Curran and A. Ross, J. Med. Chem., 17, 273 (1974)] is dissolved in 500 ml. of acetic acid with heat and stirring. A 56 ml. portion of liquid bromine is dissolved in 500 ml. of acetic acid and added dropwise to the above solution over a two hour period. The mixture is then heated at steam bath temperature for ½ hour, poured onto crushed ice and filtered. The solid is washed with water and dried in vacuo, giving 184 g. of p-(1,6-dihydro-4-methyl-6-oxo-3-pyridazinyl)benzonitrile.

A mixture of 184 g. of the above benzonitrile and 900 ml. of phosphorous oxychloride is heated on a steam bath for 3.5 hours. The excess phosphorous oxychloride is decomposed by slowly adding the mixture to crushed ice with stirring. The resulting solid is collected, washed with water and dried giving 199 g. of 3-chloro-5-methyl-6-(p-cyanophenyl)pyridazine, which is further purified by recrystallization from chloroform.

A 12.6 g. portion of ethyl carbazate is dissolved in 300 ml. of butanol. A 13.77 g. portion of 3-chloro-5-methyl-6-(p-cyanophenyl)pyridazine is added and the mixture is stirred at reflux for 18 hours. The mixture is cooled in ice and the solid is recovered by filtration and air dried, giving 6.3 g. of the desired product as a cream colored solid, m.p. >300° C.

EXAMPLE 2

7-Methyl-6-(m-nitrophenyl)-1,2,4-triazolo[4,3-b]pyridazin-3(2H)-one

A mixture comprising 7.0 g. of 3-chloro-5-methyl-6-(m-nitrophenyl)-pyridazine (U.S. Pat. No. 4,092,311), 5.8 g. of ethyl carbazate and 60 ml. of butanol is refluxed for 18 hours, then cooled in an ice bath and filtered. The solid is air dried giving 2.96 g. of the desired product as a yellow solid, m.p. >300° C.

EXAMPLE 3 p-(2,3-Dihydro-7-methyl-3-oxo-1,2,4-triazolo[4,3-b]pyridazin-6-yl)-thiobenzamide A 1.0 g. portion of p-(2,3-dihydro-7-methyl-3-oxo-1,2,4-triazolo[4,3-b]pyridazin-6-yl)-benzonitrile is partially dissolved in a mixture of 2.0 ml. of triethylamine 20 ml. of pyridine. Hydrogen sulfide gas is bubbled into the mixture for 3 hours. The mixture is filtered and the filtrate is cooled in ice giving a solid which is washed with petroleum ether and suction dried. This solid is boiled in 100 ml. of methanol and filtered. The solid is dried, giving 0.65 g. of the desired product as a yellow solid, m.p. 325°–329° C.

EXAMPLE 4

6-(p-Bromophenyl)-1,2,4-triazolo[4,3-b]pyridazin-3(2H)-one

A mixture of 2.69 g. of 6-(p-bromophenyl)-3-chloropyridazine (U.S. Pat. No. 4,092,311), 3.12 g. of ethyl carbazate and 50 ml. of n-butanol is heated at reflux for 16 hours, then cooled and filtered giving an orange solid which is saved. The filtrate is heated at reflux for 23 hours, then chilled in an ice bath and filtered giving more orange solid. The two crops are combined and recrystallized from dimethylformamide, giving 0.65 g. of the desired product as orange crystals, m.p. 348°–350° C. (dec.).

EXAMPLE 5

2,7-Dimethyl-6-(m-nitrophenyl)-1,2,4-triazolo[4,3-b]pyridazin-3(2H)-one

A suspension of 3.0 g. of 7-methyl-6-(m-nitropheyl)-1,2,4-triazolo[4,3-b]pyridazin-3(2H)-one in 30 ml. of dry dimethylformamide is stirred for 10 minutes. A 0.54 g. portion of a 50% oil suspension of sodium hydride is added and the mixture is stirred for ½ hour with cooling. A 0.75 ml. portion of methyl iodide is added, the mixture is stirred for one hour and then filtered. The solid is washed with water and dried, giving 2.12 g. of the desired product as a yellow solid, m.p. 250°–253° C.

EXAMPLE 6

6-(m-Aminophenyl)-2,7-dimethyl-1,2,4-triazolo[4,3-b]pyridazin-3(2H)-one

A mixture of 5.0 g of 2,7-dimethyl-6-(m-nitrophenyl)-1,2,4-triazolo[4,3-b]pyridazin-3(2H)-one, 50 ml. of trifluoroacetic acid and a catalytic amount of 10% palladium on carbon are shaken in a Parr bottle under 40 lb. pressure of hydrogen for 2 hours and then filtered. The filtrate is concentrated in vacuo to an oil which is dissolved in 50 ml. of water and adjusted to pH 4.7 with 5N sodium hydroxide. The resulting solid is collected by filtration and air dried, giving 3.6 g. of the desired product as a green solid, m.p. 192°–195° C.

EXAMPLE 7

6-(p-Bromophenyl)-2-ethyl-7-methyl-1,2,4-triazolo[4,3-b]pyridazin-3(2H)-one

A mixture comprising 328 g. of 3-(p-bromophenyl)-6-chloro-4-methylpyridazine (U.S. Pat. No. 4,092,311), 242 g. of ethyl carbazate and 2 liters of butanol is stirred at reflux for 4 days, then cooled in an ice bath. The resulting solid is collected by filtration and air dried, giving 269 g. of 6-(p-bromophenyl)-7-methyl-1,2,4-triazolo[4,3-b]pyridazin-3(2H)-one.

A 10.0 g. portion of the above product is dissolved in 300 ml. of dry dimethylformamide and then filtered. To the filtrate is added 1.64 g. of a 50% oil dispersion of sodium hydride and the mixture is stirred for one hour. A 2.9 ml. portion of ethyl iodide is added dropwise with stirring over 10 minutes and then the mixture is stirred overnight. Charcoal is used to filter the mixture and the filtrate is concentrated in vacuo to an oil. Trituration with water gives the desired product as 8.6 g. of a yellow solid, m.p. 164°–167° C.

EXAMPLE 8

6-(3,4,5-Trimethoxyphenyl)-1,2,4-triazolo[4,3-b]pyridazin-3(2H)-one

A mixture of 99.4 g. of 3,4,5-trimethoxybenezaldehyde, 112 g. of p-toluenesulfonic acid, 106 g. of morpholine, 39.1 g. of potassium cyanide and 500 ml. of tetrahydrofuran is reacted to give 138.6 g. of α-(3,4,5-trimethoxyphenyl)-4-morpholineacetonitrile.

A 101.1 g. portion of the above product is dissolved in 1500 ml. of dry tetrahydrofuran and then filtered. To the filtrate is added 10 ml. of 30% potassium hydroxide in ethanol dropwise, with stirring. The mixture is stirred for 10 minutes, then 50 ml. of ethyl acrylate is added dropwise and the mixture is stirred overnight. The mixture is concentrated free of solvent and the concentrate is taken down with toluene, stirred with petroleum ether and the solid is recovered by filtration. This process is repeated twice. The final concentrate is taken down with toluene several times and then allowed to stir with petroleum ether. The resulting solid is dried giving 105.6 g. of γ-cyano-γ-(3,4,5-trimethoxyphenyl)-4-morpholinebutyric acid ethyl ester.

A mixture of 105.6 g. of the above ester, 15.6 ml. of hydrazine hydrate and 1100 ml. of ethanol is heated at reflux for 2 days, clarified through charcoal and the filtrate cooled in ice, giving 39.9 g. of 4,5-dihydro-6-(3,4,5-trimethoxyphenyl)-3(2H)-pyridazinone as a cream colored solid.

A mixture of 39.9 g. of the above pyridazinone, 38.2 g. of sodium m-nitrobenzene sulfonate, 27.2 g. of sodium hydroxide and 400 ml. of water is heated on a steam bath for 3 hours and treated while hot with charcoal. The filtrate is cooled in ice and then made acidic with concentrated hydrochloric acid. The resulting solid is collected by filtration, washed with water and dried, giving 31.19 g. of 6-(3,4,5-trimethoxyphenyl)-3(2H)-pyridazinone as a yellow solid.

A mixture of 31.19 g. of 6-(3,4,5-trimethoxyphenyl)-3(2H)-pyridazinone and 300 ml. of phosphorous oxychloride is heated on a steam bath for 18 hours and then concentrated free of phosphorous oxychloride to an oil. The oil is triturated with ice water, giving a solid which is collected by filtration, washed with water and dried, giving 30.0 g. of 3-chloro-6-(3,4,5-trimethoxyphenyl)-pyridazine A mixture of 5.0 g. of the above pyridazine, 3.7 g. of ethyl carbazate and 100 ml. of butanol is stirred at reflux for 3 days, then cooled in ice giving a solid which is dried giving the desired product as a cream colored solid, m.p. 289°–290° C.

EXAMPLE 9

6-(3-Fluoro-4-methoxyphenyl)-1,2,4-triazolo[4,3-b]pyridazin-3(2H)-one

A mixture comprising 4.0 g. of 3-chloro-6-(3-fluoro-4-methoxyphenyl)-pyridazine (U.S. Pat. No. 4,092,311), 3.54 g. of ethyl carbazate and 100 ml. of butanol is stirred at reflux for 3 days and then cooled in an ice bath. The resulting solid is collected by filtration and dried, giving 2.4 g. of the desired product as a tan solid, m.p. 289°–290° C.

EXAMPLE 10

6-(3,4-Dichlorophenyl)-1,2,4-triazolo[4,3-b]pyridazin-3(2H)-one

A mixture of 3,4-dichlorobenzaldehyde, p-toluenesulfonic acid, morpholine and sodium cyanide in tetrahydrofuran is reacted to give α-(3,4-dichlorophenyl)-4-morpholineacetonitrile.

A 136.9 g. portion of the above product is dissolved in 600 ml. of tetrahydrofuran with stirring. To this is added dropwise 10 ml. of 30% potassium hydroxide in ethanol. A 25 ml. portion of ethyl acrylate is added dropwise over a 10 minute period, then the mixture is stirred for 2 hours. This procedure is repeated and the reaction mixture is concentrated free of solvent and taken down with toluene several times giving an oil. This oil is diluted with ether, filtered, concentrated, vacuum distilled, diluted with ether, treated with charcoal, and the filtrate is concentrated, giving 132.6 g. of γ-cyano-γ-(3,4-dichlorophenyl)-4-morpholinebutyric acid ethyl ester as an oil.

A mixture of 132.6 g. of the above ester, 36 ml. of hydrazine hydrate and 500 ml. of ethanol is stirred at reflux for 7 days. The resulting solid is recovered by filtration and washed with water, giving 63.45 g. of 4,5-dihydro-6-(3,4-dichlorophenyl)-3(2H)-pyridazinone.

A mixture of 63.45 g. of the above pyridazinone, 67.5 g. of sodium m-nitrobenzene sulfonate, 52.0 g. of sodium hydroxide and 2 liters of water is heated on a steam bath overnight, then filtered. The filtrate is treated with charcoal and this filtrate is rendered acidic with concentrated hydrochloric acid. The resulting solid is collected by filtration, washed with water and dried, giving 26.4 g. of 6-(3,4-dichlorophenyl)-3(2H)-pyridazinone.

A mixture of 10.0 g. of 6-(3,4-dichlorophenyl)-3(2H)-pyridazinone and 100 ml. of phosphorous oxychloride is heated on a steam bath for 3 days and then concentrated free of solvent. The oily concentrate is stirred with ice water and the solid is filtered, washed with water and dried. This product is purified by column chromatography, giving 5.5 g. of 3-chloro-(3,4-dichlorophenyl)-pyridazine.

A mixture of 3.0 g. of the above pyridazine, 6.03 g. of ethyl carbazate and 75 ml. of butanol is stirred at reflux for 48 hours, then concentrated free of solvent and the concentrate stirred with ice water. The resulting solid is filtered, washed with water and dried. This solid is heated in a bath at 230° C. for one hour giving a dark brown solid. This solid is boiled in chloroform, filtered and air dried giving 2.0 g. of the desired product as a tan solid, m.p. 336°-338° C.

EXAMPLE 11

6-(p-Chlorophenyl)-8-methyl-1,2,4-triazolo[4,3-b]pyridazin-3(2H)-one

A 35.50 g. portion of 3-p-chlorobenzoyl-2-methyl propionic acid, 85 ml. of hydrazine hydrate and 400 ml. of ethanol are stirred at reflux for 18 hours, concentrated to ¾ original volume, cooled in ice and the solid is filtered giving 31.32 g. of 4,5-dihydro-4-methyl-6-(p-chlorophenyl)-3(2H)-pyridazinone.

A 31.32 g. portion of the above pyridazinone is dissolved in 250 ml. of acetic acid. An 8.2 ml. portion of bromine is dissolved in 50 ml. of acetic acid and 25 ml. of this solution is added to the reaction mixture. The reaction mixture is heated until all the bromine color is gone, then the rest of the bromine solution is added with stirring over a 20 minute period. The mixture is heated on a steam bath for ½ hour and then diluted with ice water. The resulting solid is filtered, washed with water and air dried, giving 29.9 g. of 6-(p-chlorophenyl)-4-methyl-3(2H)-pyridazinone.

A 15.0 g. portion of the above pyridazinone in 200 ml. of phosphorous oxychloride is heated on a steam bath for 18 hours, then concentrated free of solvent. The concentrate is stirred with cold water, filtered and the solid washed with water and air dried, giving 15.95 g. of 3-chloro-6-(p-chlorophenyl)-4-methylpyridazine.

A mixture comprising 2.0 g. of the above pyridazine, 1.87 g. of ethyl carbazate and 60 ml. of butanol is stirred at reflux for 48 hours, then cooled in an ice bath. The resulting solid is filtered, washed with petroleum ether and dried, giving 1.2 g. of the desired product as a tan solid, m.p. 278°-280° C.

We claim:
1. The method of meliorating asthmatic conditions in a mammal which comprises administering to said mammal an effective amount of a compound of the formula:

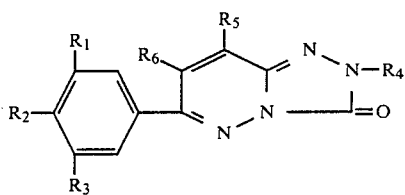

wherein $R_1$, $R_2$ and $R_3$ are each individually selected from the group consisting of hydrogen, fluoro, chloro, bromo, cyano, nitro, amino, alkoxy having up to 6 carbon atoms, trifluoromethyl and thiocarbamoyl with the proviso that at least one of $R_1$, $R_2$ and $R_3$ must be other than hydrogen; and $R_4$, $R_5$ and $R_6$ are each individually selected from the group consisting of hydrogen and alkyl having up to 6 carbon atoms.

2. The compound 6-(3,4,5-trimethoxyphenyl)-1,2,4-triazolo[4,3-b]pyridazin-3(2H)-one.

3. The compound 6-(3-fluoro-4-methoxyphenyl)-1,2,4-triazolo[4,3-b]pyridazin-3(2H)-one.

* * * * *